United States Patent [19]

Drabb, Jr.

[11] Patent Number: 5,847,140

[45] Date of Patent: Dec. 8, 1998

[54] INTERMEDIATES FOR THE MANUFACTURE OF HERBICIDAL 1-{ [2-(CYCLOPROPYLCARBONYL) PHENYL] SULFAMOYL}-3-(4,6-DIALKOXY-2-PYRIMIDINYL) UREA COMPOUNDS

[75] Inventor: Thomas Walter Drabb, Jr., Trenton, N.J.

[73] Assignee: American Cyanamid Company, Madison, N.J.

[21] Appl. No.: 465,049

[22] Filed: Jun. 6, 1995

[51] Int. Cl.⁶ .................................................. C07D 239/42
[52] U.S. Cl. .............................................................. 544/332
[58] Field of Search ............................................... 544/332

[56] References Cited

U.S. PATENT DOCUMENTS

| | | | |
|---|---|---|---|
| 3,939,158 | 2/1976 | Begrich | 260/249.5 |
| 4,401,816 | 8/1983 | Levitt | 544/320 |
| 4,622,065 | 11/1986 | Van Gemert | 71/93 |
| 4,696,695 | 9/1987 | Gemert | 71/92 |
| 4,741,762 | 5/1988 | Van Gemert | 71/92 |
| 5,009,699 | 4/1991 | Brady et al. | 71/92 |
| 5,280,007 | 1/1994 | Kawai | 504/105 |
| 5,414,136 | 5/1995 | Cortes | 568/306 |
| 5,492,884 | 2/1996 | Condon et al. | 504/214 |
| 5,559,234 | 9/1996 | Drabb | 544/321 |
| 5,599,996 | 2/1997 | Condon et al. | 564/442 |

FOREIGN PATENT DOCUMENTS

| | | | |
|---|---|---|---|
| 679646 | 11/1995 | European Pat. Off. | C07D 239/52 |
| 4337847 | 5/1995 | Germany | C07D 239/47 |
| 4414476 | 11/1995 | Germany | C07D 239/52 |

OTHER PUBLICATIONS

D. Brown et al., The Chemistry if Heterocyclic Compounds, vol. 52 (The Pyridines), 397–401, J. Wiley & Sons, NY 1994.

*Primary Examiner*—John M. Ford
*Attorney, Agent, or Firm*—Charles F. Costello

[57] ABSTRACT

There is provided an effective and efficient, three step process for the manufacture of crop-selective, herbicidal 1-{[2- (cyclopropylcarbonyl)-phenyl]sulfamoyl}-3-(4,6-dialkoxy-2-pyrimidinyl)urea compounds, and an intermediate for use therein.

3 Claims, No Drawings

INTERMEDIATES FOR THE MANUFACTURE OF HERBICIDAL 1-{ [2-(CYCLOPROPYLCARBONYL) PHENYL] SULFAMOYL}-3-(4,6-DIALKOXY-2-PYRIMIDINYL) UREA COMPOUNDS

BACKGROUND OF THE INVENTION

1-{[2-(Cyclopropylcarbonyl)phenyl]sulfamoyl}-3-(4,6-dialkoxy-2-pyrimidinyl)urea compounds which are useful as crop-selective herbicidal agents are disclosed in U.S. Pat. Nos. 5,009,699 and 5,280,007. In particular, 1-{[o-(cyclopropylcarbonyl)phenyl]-sulfamoyl}-3-(4,6-dimethoxy-2-pyrimidinyl)urea is being developed as a herbicide for control of a wide range of dicot and sedge weed species infesting cereals and rice. Additionally, 1-{[o-(cyclopropylcarbonyl)-phenyl]sulfamoyl}-3-(4,6-dimethoxy-2-pyrimidinyl)urea binds tightly to soil and would not be expected to pose a threat to groundwater by leaching from soil. Further, 1-{[o-(cyclopropylcarbonyl)phenyl]sulfamoyl}-3-(4,6-dimethoxy-2-pyrimidinyl)urea has been shown to be very safe for mammals and other non-target organisms.

Since 1-{[2-(cyclopropylcarbonyl)phenyl]-sulfamoyl}-3-(4,6-dialkoxy-2-pyrimidinyl)urea compounds are highly active, crop-selective herbicidal agents and are environmentally benign, there is ongoing research to discover and develop effective and efficient processes for their manufacture.

U.S. Pat. No. 4,401,816 discloses sulfamoyl chlorides which are useful in the preparation of sulfamides and pyrrole sulfonamides. However, that patent does not disclose a process for the preparation of sulfamoyl urea compounds.

U.S. Pat. No. 3,939,158 discloses N-(2,4-dihalo-s-triazin-6-yl)ureas and a process for their manufacture. However, the patentee does not describe a process for the preparation of sulfamoyl urea compounds.

It is therefore an object of the present invention to provide an effective and efficient process for the manufacture of 1-{[2-(cyclopropylcarbonyl)phenyl]-sulfamoyl}-3-(4,6-dialkoxy-2-pyrimidinyl)urea compounds.

It is also an object of the present invention to provide intermediate compounds which are useful in the process of the present invention.

SUMMARY OF THE INVENTION

The present invention relates to an effective and efficient, three step process for the manufacture of a 1-{[2-(cyclopropylcarbonyl)phenyl]sulfamoyl}-3-(4,6-dialkoxy-2-pyrimidinyl)urea having the structural formula I

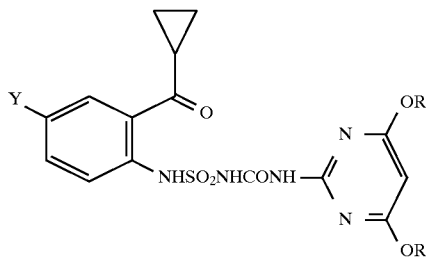

wherein
Y is hydrogen, halogen, $C_1$–$C_4$alkyl or $C_1$–$C_4$haloalkyl; and
R is $C_1$–$C_6$alkyl, which comprises reacting a 2-amino-4,6-dihalopyrimidine having the structural formula II

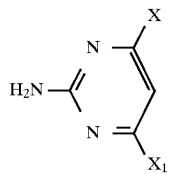

where X and $X_1$ are each independently Cl, Br or I with chlorosulfonyl isocyanate in the presence of a first solvent to obtain an intermediate compound, reacting the intermediate compound in situ with a 2-aminophenyl cyclopropyl ketone having the structural formula III

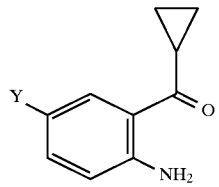

wherein Y is as described above and a base to form a 1-{[2-(cyclopropylcarbonyl)phenyl]sulfamoyl}-3-(4,6-dihalo-2-pyrimidinyl)urea having the structural formula IV

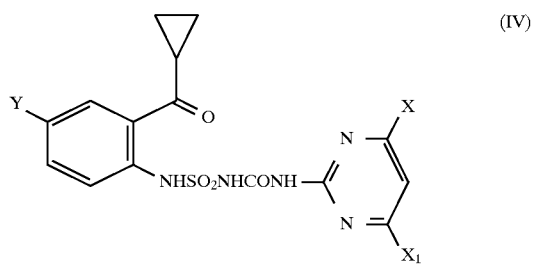

wherein Y, X and $X_1$ are as described above, and reacting the formula IV urea with at least about two molar equivalents of an alkali metal alkoxide having the structural formula V $$RO^-M^+ \quad\quad (V)$$

wherein M is an alkali metal and R is as described above in the presence of a second solvent to form the desired formula I compound.

The present invention also relates to 1-{[2-(cyclopropylcarbonyl)phenyl]sulfamoyl}-3-(4, 6-dihalo-2-pyrimidinyl)ureas having the structural formula IV

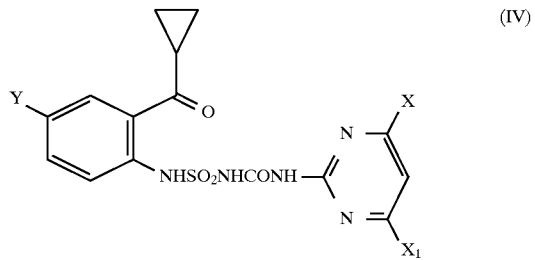

wherein
Y is hydrogen, halogen, $C_1$–$C_4$alkyl or $C_1$–$C_4$haloalkyl; and
X and $X_1$ are each independently Cl, Br or I. The formula IV compounds are useful as intermediate compounds in the manufacture of the crop-selective 1-{[2-(cyclopropylcarbonyl)phenyl]sulfamoyl}-3-(4,6-dialkoxy-2-pyrimidinyl)urea herbicidal agents.

DETAILED DESCRIPTION OF THE INVENTION

Weeds cause tremendous global economic losses by reducing crop yields and lowering crop quality. In the United States alone, agronomic crops must compete with hundreds of weed species. Advantageously, it has recently been discovered that 1-{[2-(cyclopropylcarb-onyl)phenyl]sulfamoyl}-3-(4,6-dialkoxy-2-pyrimidin-yl)ureas are highly active herbicidal agents. Those compounds, especially 1-{[o-(cyclopropylcarbonyl)-phenyl]sulfamoyl}-3-(4,6-dimethoxy-2-pyrimidinyl)urea, are particularly useful for the selective control of weeds in the presence of crops.

Advantageously, it has now been found that the crop-selective herbicidal agents of formula I may be obtained in high yield and good purity by the effective and efficient, three step process of the present invention.

One of the preferred embodiments of the present invention involves reacting a formula II 2-amino-4,6-dihalopyrimidine as described above with at least about one molar equivalent of chlorosulfonyl isocyanate in the presence of a first solvent preferably at a temperature range of about −20° C. to 10° C., more preferably about −5° C. to 5° C., to form an intermediate compound, reacting the intermediate compound in situ with at least about one molar equivalent of a formula III 2-aminophenyl cyclopropyl ketone as described above and at least about one molar equivalent, preferably about one to three molar equivalents of a base at a temperature range of about −20° C. to 30° C., more preferably about −5° C. to 15° C. to form a formula IV 1-{[2-(cyclopropylcarbonyl)phenyl]sulfamoyl}-3-(4,6-dihalo-2-pyrimidinyl)urea as described above, and reacting the formula IV urea with at least about two molar equivalents, preferably about two to four molar equivalents of a formula V alkali metal alkoxide as described above in the presence of a second solvent preferably at a temperature range of about 20° C. to 100° C., more preferably about 40° C. to 80° C., to form a 1-{[2-(cyclopropylcarbonyl)phenyl]sulfamoyl}-3-(4,6-dialkoxy-2-pyrimidinyl)urea of formula I.

The product formula I compounds may be isolated by conventional techniques such as acidification and dilution of the reaction mixture with water followed by filtration of the formula I product or extraction of the product with a suitable solvent.

The process of the present invention is especially useful for the preparation of 1-{[o-(cyclopropylcarbon-yl)phenyl]sulfamoyl}-3-(4,6-dimethoxy-2-pyrimidinyl)-urea; and 1-{[2-(cyclopropylcarbonyl)-4-fluorophenyl]-sulfamoyl}-3-(4,6-dimethoxy-2-pyrimidinyl)urea.

Surprisingly, it has been found that 1-{[2-(cyclopropylcarbonyl)phenyl]sulfamoyl}-3-(4,6-dihalo-2-pyrimidinyl)urea compounds of formula IV are important intermediates in the manufacture of the crop-selective herbicidal agents of formula I. Formula IV compounds which are particularly suitable for use in the process of the present invention include 1-{[o-(cyclopropyl-arbonyl)phenyl]sulfamoyl}-3-(4,6-dichloro-2-pyrimidinyl)urea; and 1-{[2-(cyclopropylcarbonyl)-4-fluorophenyl]sulfamoyl}-3-(4,6-dichloro-2-pyrimidin-yl)urea, among others.

Alkali metals which are suitable for use in the process of the present invention include sodium, potassium and lithium with sodium and potassium being preferred. Bases suitable for use in the invention process include organic bases such as tri($C_1$–$C_4$-alkyl)amines, pyridine, substituted pyridines, quinoline, substituted quinolines, and the like with tri($C_1$–$C_4$alkyl)amines such as triethylamine being preferred.

First solvents suitable for use in the above process include inert, nonprotic solvents such as halogenated aliphatic hydrocarbons such as methylene chloride and ethylene dichloride, aromatic hydrocarbons such as toluene, ethers such as ethyl ether and tetrahydrofuran, and the like with halogenated aliphatic hydrocarbons such as methylene chloride and ethylene dichloride being preferred. Second solvents suitable for use in the process of the present invention include tetrahydrofuran, N,N-dimethylformamide, dioxane, ROH alcohols wherein R corresponds to the R group described above for formula V, and the like with ROH alcohols such as methanol being preferred.

In order to facilitate a further understanding of the invention, the following examples are presented to illustrate more specific details thereof. The invention is not to be limited thereby except as defined in the claims.

EXAMPLE 1

Preparation of 1-{[o-(Cyclopropylcarbonyl)-phenyl]sulfamoyl}-3-(4,6-dichloro-2-pyrimidinyl)Urea

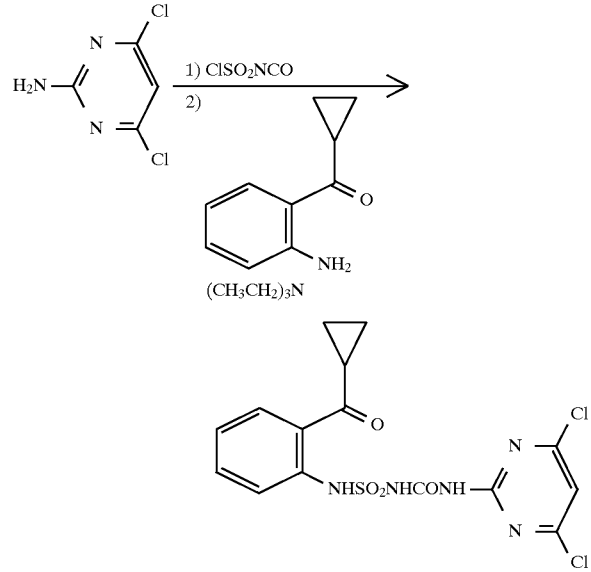

2-Amino-4,6-dichloropyrimidine (6.15 g, 0.0375 mol) is added portionwise to a solution of chlorosulfonyl isocyanate (5.30 g, 0.0375 mol) in methylene chloride at 0° C. The resulting mixture is stirred at 0° to 2° C. for two hours and a solution of o-aminophenyl cyclopropyl ketone (6.04 g, 0.0375 mol) and triethylamine (3.8 g, 0.0406 mol) in methylene chloride is slowly added to the mixture. The resulting solution is stirred at room temperature overnight, washed with water, dried over anhydrous magnesium sulfate and concentrated in vacuo to obtain the title product as a yellow solid (14.3 g, 75% real by HPLC analysis, 68% yield) which is used as a starting material for Example 2 without purification. A portion of the yellow solid is purified to yield the title product, mp 114°–116° C.

EXAMPLE 2

Preparation of 1-{[o-(Cyclopropylcarbonyl)-Phenyl]sulfamoyl}-3-(4,6-dimethoxy-2-pyrimidin-yl)urea

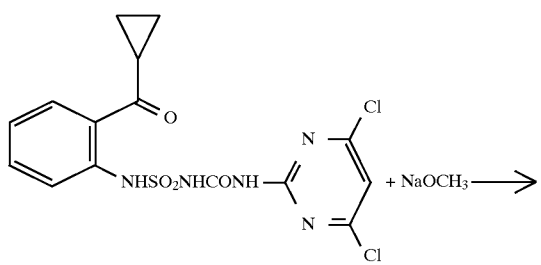

+ NaOCH₃ →

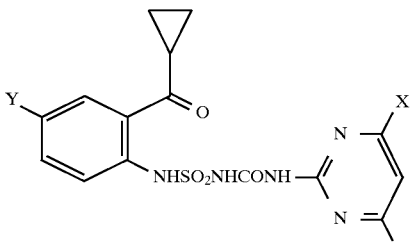

A mixture of sodium methoxide (1.08 g, 0.02 mol) in methanol is added slowly to a mixture of 1-{[o-(cyclopropyl)phenyl]sulfamoyl}-3-(4,6-dichloro-2-pyrimidinyl)urea from Example 1(4.30 g, 0.01 mol) in methanol at 60° C. The reaction mixture is heated at 60° C. for two hours, cooled, treated with additional sodium methoxide (0.54 g), refluxed overnight, cooled, acidified and concentrated in vacuo to obtain a residue. The residue is slurried in methanol, filtered, washed sequentially with methanol and water, and dried in a vacuum oven at 55°–60° C. to give the title product as a cream colored solid (2.2 g, 98.6% real by HPLC analysis, 70% yield, mp 168.5°–169.5° C.).

I claim:

1. A compound having the structural formula wherein

Y is hydrogen or F; and X and $X_1$ are Cl.

2. The compound according to claim 1 1-{[o-(cyclopropylcarbonyl)phenyl]sulfamoyl}-3-(4,6-dichloro-2-pyrimidinyl)urea.

3. The compound according to claim 1 1-{[2-(cyclopropylcarbonyl)-4-fluorophenyl]sulfamoyl}-3-(4,6-dichloro-2-pyrimidinyl)urea.

* * * * *